United States Patent [19]
Pickenhagen et al.

[11] Patent Number: 5,892,059
[45] Date of Patent: Apr. 6, 1999

[54] PROCESS FOR PRODUCING A ROSE OXIDE

[75] Inventors: Wilhelm Pickenhagen, Höxter; Dietmar Schatkowski, Stadtoldendorf, both of Germany

[73] Assignee: Dragoco Gerberding & Co. Aktiengesellschaft, Germany

[21] Appl. No.: 966,185

[22] Filed: Nov. 7, 1997

[30] Foreign Application Priority Data

Nov. 8, 1996 [DE] Germany .......................... 196 45 922.2

[51] Int. Cl.$^6$ .......................... C07C 27/04; C07D 309/04
[52] U.S. Cl. ............................................ 549/356; 568/885
[58] Field of Search ............................... 549/356; 568/885

[56] References Cited

U.S. PATENT DOCUMENTS 4,429,144  1/1984  Hoffman .

*Primary Examiner*—Johann Richter
*Assistant Examiner*—Taofiq A. Solola
*Attorney, Agent, or Firm*—Pendorf & Cutliff

[57] ABSTRACT

An improved process for production of an isomer mixture of Z- and E-2-[2-Methyl-prop-1-en-1-yl-]-4-methyl-tetrahydropyran, more commonly known under the name cis- and trans-rose oxide, which as a rule contains at least 80% of the natural Z-isomers (cis-rose oxide) which are valuable in the perfume industry.

15 Claims, 2 Drawing Sheets

PROCESS FOR PRODUCING A ROSE OXIDE

Process for Production of an Isomer Mixture of Z- and E-2-[2-Methyl-prop-1-en-1-yl-]-4-methyl-tetrahydropyran of General Formula A

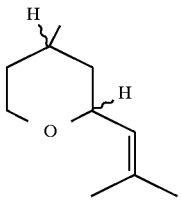

(A)

The invention concerns an improved process for production of an isomer mixture of Z- and E-2-[2-Methyl-prop-1-en-1-yl-]-4-methyltetrahydropyran of the General Formula A, more commonly known under the name cis- and trans-rose oxide, which as a rule contains at least 80% of the natural Z-isomers (cis-rose oxide) which are valuable in the perfume industry. This isomer mixture will hereafter also be referred to as "rose oxide of General Formula A"; this concept includes racemic as well as optically active isomer mixtures.

The general concept "rose oxide" includes in the framework of this application, besides the inventive isomer mixture ("rose oxide of General Formula A") with as a rule at least 80% of the Z-isomer, also other mixtures of the Z- and E-isomers as well as the pure isomer and enantiomer.

Since the isolation [C. Seidel, M. Stoll, Helv. Chim. Acta, 42, 1830 (1959); Y. Naves, D. Lamparsky, P. Ochsner, Bull. Soc. Chim. Fr., 645 (1961)] and structural identification [Y. Naves, D. Lamparsky, P. Ochsner, Bull. Soc. Chim. Fr., 645 (1961); C. Seidel, D. Felix, A. Eschenmoser, K. Bieman, E. Palluy and M. Stoll, Helv. Chim. Acta, 44, 598 (1961)] of rose oxide there have occurred numerous publications, which concerned new synthesis processes for the production thereof.

So there is described for example in EP 00211769 and in Tetrahendon Letters 39, 3599–3602 (1971) of T. Schono, A. Ikeda, Y. Kimura the electro-chemical production of optically active or, as the case may be, racemic rose oxide, beginning with optically active or as the case may be racemic citronellol.

Further synthesis begin with 3-Methyl-but-2-en-1-al and 2-methyl-but-1-en-4-ol [J. H. P. Tyman, B. J. Willis, Tetrahedron Letters 51, 4507 (1970)] and Epoxy-β-citronellol [G. Ohloff, B. Lienhardt, Helv. Chim. Acta 182–189 (1964)].

In DE 3150234 there is a report of a process for production of a mixture of at least 80% cis- and at most 20% trans-rose oxide, wherein the process is comprised therein, that 2-[2-methyl-prop-1-en-1-yl]-4-methylene-tetrahydropyran is hydrated with a platinum dioxide or a platinum/charcoal catalyst in the presence of a strongly acidic cation exchanger.

G. Ohloff, E. Klein, G. Schade are named as inventors of the process in DE 1137730 and DE 1443338 of the Studiengesellschaft Kohle mbH, which converts (+) and (−)- as well as racemic citronellol (1) by photochemical sensitized singlet-oxygen-oxidation in a mixture of two peroxides (2a/b) and these in a known manner [L. -F. Tietze, Th. Eicher, 428–430, (1981), Jord. Stein Publishers. Stuttgart, New York] are reduced with $Na_2SO_3$ to a mixture two diols 3a/b. By treatment of this mixture with dilute acids then only 3a (Scheme 1) is converted to a mixture of the cis- and trans-rose oxide 4. This process is described again in great detail by G. Ohloff, E. Klein and G. O. Schenck in Angew. Chem. 73, 578 (1961). Thereby one obtains, depending upon selection of appropriate citronellols, beginning with (−)-citronellol the (−)-rose oxide, from (+)-citronellol the (+)-rose oxide and beginning with racemic (+/−)-citronellol the mixture of the cis-/trans-isomer optically inactive rose oxide. In the photochemical sensitized conversion of singlet oxygen with citronellol the hydrogen atoms react with the two carbons of the isopropylidene-double bond practically equally readily, so that (after subsequent $Na_2SO_3$- reduction) and almost 1:1-mixture of the two diols (3a) and (3b) result.

Since the first investigations into the conversion of the diol-mixture 3a/b in rose oxide 4, it was always indicated [G. Ohloff, B. Lienhardt, Helv. Chim. Acta 182–189 (1964); L. -F. Tietze, Th. Eicher, 428–430, (1981), Jord. Stein Publishers, Stuttgart, N.Y.; G. Ohloff, Pure Applied Chem., 481–502, (1975)], that only the diol 3a allows itself to be converted into rose oxide.

According to G. Ohloff, E. Klein and G. O. Schenck, Angew. Chem. 73, 578 (1961) the diol (3b) does not allow itself to be modified at room temperature, though it does at higher temperatures by means of stronger acids. Then there is obtained an oxide mixture, which contains besides the rose oxides (cis- and trans-rose oxide) primarily isomers with the isopropenyl group, so called iso-rose oxide (B).

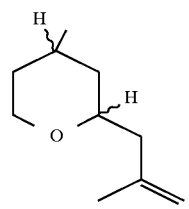

(B)

The known process, in which the production of optically active or racemic rose oxide is produced by photochemical sensitized singlet-oxygen-oxygenation of (+)- or (−)- or (+/−) citronellol, reduction of the obtained hydro-peroxide mixture (2a+2b) to the diol mixture (3a+3b) and a subsequent, according to known processes [L. -F. Tietze, Th. Eicher, 428–430, (1981), Jord. Stein Publishers, Stuttgart, New York] acid catalyzed cyclization to cis-/trans-rose oxide (Scheme 1—Compound 4), is not satisfactory for a technical application, since the 3,7-dimethyl-oct-7-en-1,6-diol (3b) which is produced to about 40–45% in the second process step of this process does not allows itself, or only under drastic conditions, to be converted to rose oxide, such that substantial proportions of the so-called iso-rose oxide (B) result, see above [G. Ohloff, E. Klein, G. O. Schenck, Angew. Chem. 73, 578 (1961)].

The known protocol [L. -F. Tietze, Th. Eicher, 428–430, (1981), Jord. Stein Publishers, Stuttgart, New York] produces then in approximately 39% yield of the corresponding rose oxide; a conversion of the diols (3b) however does not occur (or occurs only in negligible quantities).

SUMMARY OF THE INVENTION

According to the described state of the art it is thus particularly surprising, that the inventive process (with variants A, B, C, D) which can be seen in Scheme 2 and which are described in greater detail below, makes possible the conversion of 3,7-dimethyl-oct-7-en-1,6-diol (3b) individually or in mixtures with 3,7-dimethyl-oct-5-en-1,7-diol (3a) into rose oxide (5a/b) [Z-/E-2-(2-methyl-prop-1-en-1-yl)-4-methyl-tetrahydro-pyran]. The rose oxide (5a/b) corresponds to the rose oxide of General Formula A.

In the process according to the invention for the production of rose oxide of the General Formula A 3,7-dimethyl-oct-7-en-1,6-diol (3b) is treated with acid in the presence of a, as the case may be, in situ formed allylether, wherein the acid treatment occurs in a two phase liquid/liquid system under the influence of phase transfer catalysts or in a two phase liquid/solid system by means of an acid bound to a carrier substance. The reaction mechanistic function of the allylether herein is not fully understood at this time, its presence however is essential to achievement of a satisfactory conversion, in terms of yield, of the diol (3b) to rose oxide.

The inventive process results in isomer mixtures, which—as discussed above—as a rule contain at least 80% of the natural Z-isomers (cis-rose oxide) which are valuable in the perfume industry; frequently however even isomer mixtures with 90% or greater cis-rose oxide are achieved, which are naturally particularly advantageous.

The inventive process leads to good results, independent thereof, whether 3,7-dimethyl-oct-7-en-1,6-diol (3b) individually or in mixtures with 3,7-dimethyl-oct-5-en-1,7-diol (3a) is converted into rose oxide.

DETAILED DESCRIPTION OF THE INVENTION

Figure 1:
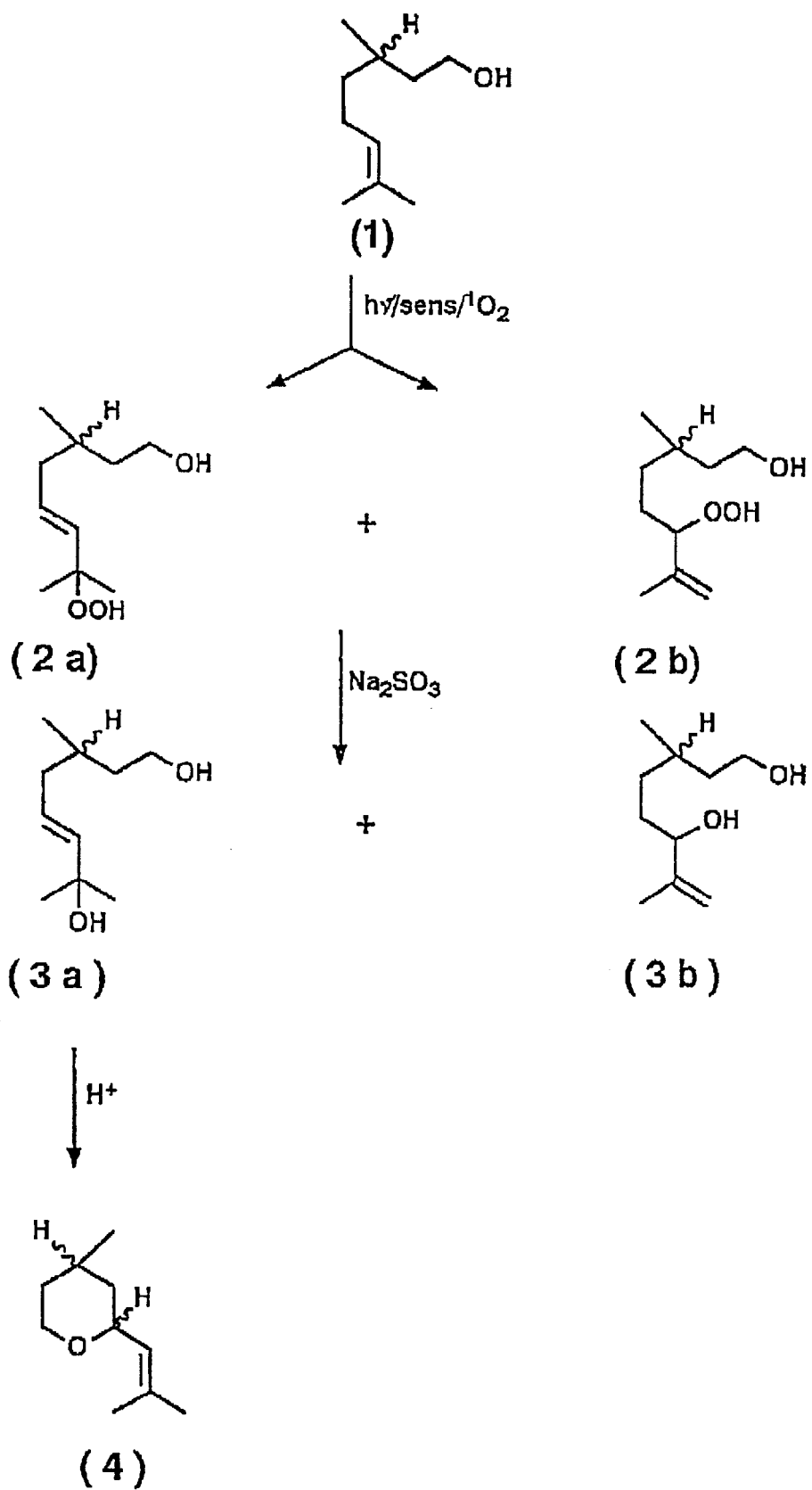
FIG. 1 shows a process which converts citronellol by photochemical sensitized singlet-oxygen-oxidation, whereby one obtains, depending upon selection of citronellols, beginning with (−)-citronellol the (−)-rose oxide, beginning with (+)-citronellol the (+)-rose oxide and beginning with racemic (+/−)-citronellol the mixture of the cis-/trans-isomer optically inactive rose oxide.
Figure 2:
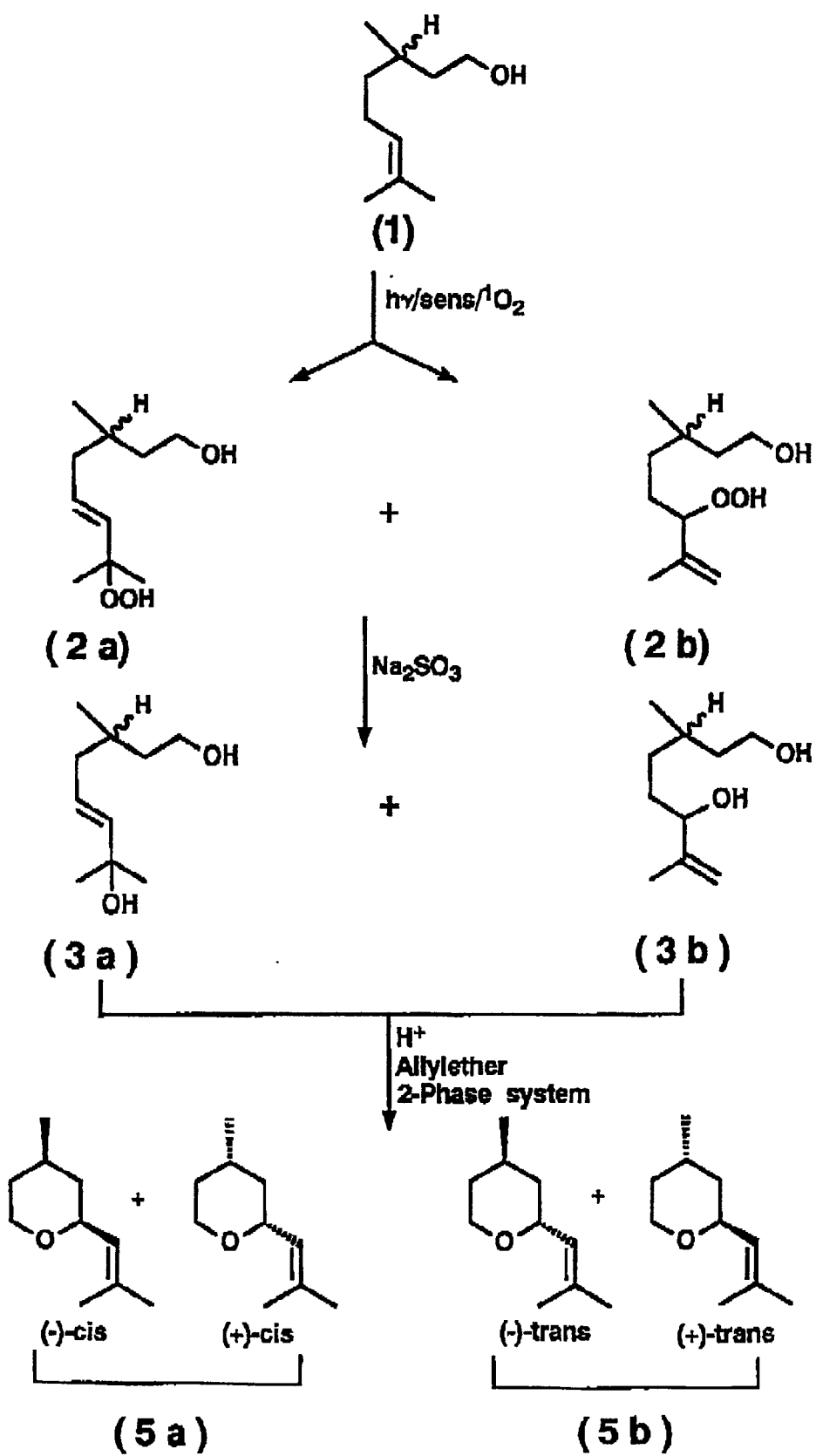
FIG. 2 shows the inventive process (with variants A, B, C, D) which makes possible the conversion of 3,7-dimethyl-oct-7-en-1,6-diol (3b) individually or in mixtures with 3,7-dimethyl-oct-5-en-1,7-diol (3a) into rose oxide (5a/b) [Z-/E-2-(2-methyl-prop-1-en-1-yl)-4-methyl-tetrahydro-pyran].

Preferably there is employed in the case of the inventive utilized allylether a rose oxide itself; this is mixed with the 3,7-dimethyl-oct-7-en-1,6-diol (3b) or the diol-mixture (3a+3b) before or during the inventive acid treatment and/or it forms itself during the acid treatment in situ from the 3,7-dimethyl-oct- 5-en-1,7-diol (3a) which, in certain cases, is present. In the presence of a rose oxide particularly good yields for the conversion of the diol (3b) to rose oxide of the General Formula A are achieved. Preferably an amount of the 3,7-dimethyl-oct-7-en-1,6-diol (3b), in certain cases mixed with the diol (3a), is mixed with an equal, larger or only slightly smaller amount of rose oxide. Such a supplementation or addition of rose oxide in more than necessary catalytic amount leads frequently to particularly good yields.

As a rule, the inventive process is carried out at elevated temperatures. In a large number of cases it is advantageous, that the reaction temperature during the acid treatment is at least for that time adjusted to the boiling point of the liquid phase; in the two phase liquid/liquid system it is adjusted to the boiling point of the lower boiling liquid phase.

For acid treatment of the diol-mixture (3a+3b) or the diol (3b) there can be employed for example sulfuric acid, phosphoric acid, and acid activated clay or Fuller's Earth, or a heteropolytungstic acid such as tungstate silicic acid or tungstate phosphoric acid may be employed.

If the inventive acid treatment is carried out in a two phase liquid/solid system by means of a carrier bound acid, then as a rule it is advantageous, when the treatment is carried out in a conventionally acid activated calcium montmorillonite (FULLER" S EARTH) such as MONTMORTILLONITE K10, MONTMORTILLONITE KSF, activated strongly acidic clay (FILTROL), activated natural calcium bentonite (KATALYSATOR KS, TONSIL OPTIMUM) and the like products available commercially. in concentrations of 0.5 to 40 weight %, preferably from 1 to 20 weight %, with respect to the employed diol mixture (3a+3b) or as the case may be diol (3b).

If the inventive acid treatment is carried out in a two phase liquid/liquid system under the conditions of a phase transfer catalysts so there can be employed in particular phase transfer catalysts as for example methyltrioctylammonium chloride (ALIQUAT), tetrabutyl ammonium-chloride-bromide or hydrogen phosphate, for example in concentrations of 0.1 weight % to 10 weight %, preferably from 4–6 weight %, with respect to the amount of the employed diol mixture (3a+3b) or the diol (3b).

If a mixture of the two diols (3a) and (3b) are employed in the inventive process, so these are preferably obtained from citronellols of the General Formula (1) for example by photochemical sensitized singlet-oxygen-oxygenation and subsequent reduction of the obtained hydroperoxide (2a+2b), see Scheme 2. To this point the known processes can be employed (see above and Scheme 1).

It is advantageous in carrying out the inventive process, to dissolve the diol mixture (3a+3b) or the diol (3b) in an aprotic solvent. As aprotic solvents, in particular pentane, hexane, heptane, cyclohexane, benzol, toluol or xylol as well as similar conventional carbohydrates and mixtures thereof can be employed.

The testing of the sensory characteristics of the iso-rose oxide (B) and mixtures of B with rose oxide (5a/b), wherein 5a/b contains greater amounts of B, showed that the iso-rose oxide (B) possesses less desirable sensory characteristics. Iso-rose oxide (B) characterizes itself by fatty-terpene, somewhat weedy or cabbage-like aspects. A presence in amounts of less than 2% in the cyclization product thus leads to a deterioration or detraction in the use of this composition as aromatic compound. G. Ohloff [G. Ohloff, Olfaction and Taste, 4, 156 (1972)] and H. Medsuda et al. [H. Medsuda et al., Flavors, Fragrances, and Essential Oils, 3, 85–91, (1995)] describe in detail the sensory characteristics of 4 optical antipodes of rose oxide. Both come to the conclusion, that in the case of the cis-compound (5a) there is a sensorily stronger and more interesting compound.

The inventive process herein comes to advantage, that one can transform the diol 3b both in mixture with as well also separate from diol 3a each according to selection of the reaction conditions under significant yield enhancement in only a single step into an at least 80% cis-rose oxide (5a). The conversion or forming of the sensory undesirable iso-rose oxide (B) occurs in the subsequent carried out process-variants A, B, C, D (Examples 3–6) in the range of <2%.

The following Examples illustrate the invention, it being understood that they do not in any way limit the invention. The indicated yields of rose oxide are with respect to the employed (−)-citronellol, (+)-citronellol and racemic (±)-citronellol.

The Examples 1 and 2 concern preferred process steps for production of racemic citronellyl-hydroperoxide (2a/b) and racemic diol mixtures (3a/b).

The Examples 3–6 (process variants A–D) each concern respectively one inventive production of racemic cis/trans-rose oxide (5a+5b) from the diol mixture 3a/b produced in accordance with Example 2.

Example 7 concerns the production of a mixture of optically active (−)-3,7-dimethyl-oct-5-en-1,7-diol and (−)-3,7-dimethyl-oct-7-en-1,6-diol; Example 8 concerns the production according to the invention of (−)-cis/trans-rose oxide beginning with this mixture.

Examples 9 and 10 concern the corresponding inventive production of a mixture of an optically active (+)-3,7-dimethyl-oct-5-en-1, 7-diol and (+)-3,7-dimethyl-oct-7-en-1,6-diol as well as the production of (+)-cis/trans-rose oxide produced in accordance with the invention from this mixture.

Example 11 concerns the production of (undesirable) diol 3,7-dimethyl-oct-7-en-1,6-diol (3b).

Example 12 concerns a non-inventive (comparative) example for production of racemic cis/trans-rose oxide from the undesirable diol (3b) according to Example 11; the Examples 13 and 14 are, in comparison, preferred inventive Examples for production of the racemic cis/trans-rose oxide from the unmixed diol (3b) wherein the inventive yield according to Example 14 is significantly higher than that according to Example 13.

EXAMPLE 1
Production of Racemic Citronellyl-Hydroperoxid (2a/b)

In an illumination device of quartz-glass with a gas inlet conduit (frit, batch) and return flow cooler 112 g (0.72 mol) of racemic citronellol synthetic, 300 ml methanol and 500 mg Rose Bengale were illuminated under introduction of an oxygen stream (approximately 700 ml/h) over a time of 15–16 hours at 20–25° C. with a 500 watt mercury high-pressure lamp.

Once obtained a photo-oxidation solution with racemic citronellyl-hydroperoxid (2a/b).

EXAMPLE 2
Production of Racemic Diol-Mixture (3a/b)

In a 1 liter 3-necked flask with return flow cooler and dropping funnel 100.8 g (0.8 mol) $Na_2SO_3$ and 300 ml of water were provided. Then one dropwise added to this within 1 hour at 50° C. the photooxidation solution produced in Example 1 (2a/b). Subsequently, this was stirred over a period of 3–4 hours at 40–50° C., and over a period of 1 hour approximately 550 ml methanol/water was distilled off. After cooling off to room temperature $H_2O$ was added, strongly stirred and the aqueous phase was separated off after precipitation.

There remained 150 g raw product (racemic diol-mixture (3a/b)).

Gaschromatogramm (Shimadzu GC 14A, DB-1, 30 m, 100–240° C., 10° C./min);

3a $R_t$=7.6'; (46%)
3b $R_t$=8.5'; (45%)

EXAMPLE 3
Production of Racemic Cis/trans-Rose Oxide (5a+5b) [9:1] Variant A

In a 2 liter 3 neck flask with funnel dropper, thermometer, return flow cooler and water separator 50 g (0.27 mol) diol-mixture 3a/b (from Example 2), 1.5 liter hexane 63/80 and 2.5 g. Filtrol® were added with mixing over a period of time of 10 hours with return flow. During this time a total of 4.8 ml water were distilled off.

After cooling to room temperature the Fitrol was filtered off and the organic phase was washed to neutral with soda solution and water. After distilling off the solvent 39 g of raw product remained (racemic cis/trans-rose oxide (5a+5b)).

GC (Conditions see Example 2): 5a (66.9%); 5b (7.4%); B=1.4%

Σ 5a+5b =74.3%
5a:5b =90:10

A distillation through a 30 cm metal packed column produced 22.1 g $KP_{22mbar}$=80°–81° C. This corresponds to a yield of 59.2%.

GC (Conditions see Example 2): 5a (90.1%); 5b (7.9%); B=0.3%

Σ 5a+5b=98.0%
5a:5b=92:8
D 20/4=0.8703
n 20/D=1.4539
[α] 20/D=0.1°

GC/MS: HP 5970 B, DBWax-60 N, 60 m, 60°–240° C., 4° C./min

5a $R_t$=15.5
MS (70 eV):m/e (%)=154 (16, M↑), 139 (100), 85 (13), 83 (28), 69 (63), 67 (11), 55 (28), 39 (15).

5a $^{13}$C-NMR $(CDCl_a)$, Varian VXR-300: [ppm]: 18.34, 22.32, 25.70 $(CH_3)$, 34.43, 40.82, 67.88 $(CH_2)$, 30.25, 74.62, 126.37 (CH), 135.05 (C).

5 b $R_t$=16.09
MS (70 ev):m/e (%)=154 (11, M⁺), 139 (100), 85 (11), 83 (26), 69 (63), 67 (11), 55 (29), 39 (15).

5b $^{13}$C-NMR $CDCl_a)$, Varian VXR-300: [ppm]=18.27, 19.23, 25.79 $(CH_3)$, 32.54, 38.21, 62.13 $(CH_2)$, 24.97, 69.10, 125.37 (CH), 135.48 (C).

B $R_t$=15.12
MS (70 eV): m/e (%)=154 (35, M⁺), 139 (100), 83 (22), 71 (50), 69 (61), 67 (23), 55 (64), 41 (79).
$R_t$=15.12
MS (70 eV): m/e (%)=154 (37, M⁺), 139 (100), 83 (23), 71 (49), 69 (68), 67 (25), 55 (62), 41 (80).

EXAMPLE 4
Production of Racemic Cis/trans-Rose Oxide (5a+5b) [9:1] Variant B

In a 1 liter stirrer with drop funnel, thermometer and return flow cooler 300 g toluol, 50 g 50% sulfuric acid, 1 g Aliquat® R 336 and 50 g (0.27 mol) diol-mixture 3a/b (from Example 2) were added with mixing over 15 minutes with return circulation, cooled to room temperature, the organic phase separated, washed to neutral with sodium solution and water, dried over sodium sulfate and the solvent distilled off under reduced pressure.

There remained 42 g raw product (racemic cis/trans-rose oxide (5a+5b)).

GC (Conditions see Example 2): 5a (66.2%); 5b (5.9%); B=0.4%

Σ 5a+b=72.4%
5a:5b=91:9

The distillation through a 30 cm metal packed column produced 22.3 g $KP_{22mbar}$=80° C.–81.5° C. This corresponds to a yield of 59.8%.

GC (Conditions see Example 2): 5a (90.0%); 5b (7.8%); B=0.35%

Σ 5a+5b=97.8%
5a:5b=92:8
D 20/4=0.8699
n 20/D=1.4540
[α] 20/d=0.1°

GC/MS: Conditions see Example 3
5a $R_t$=15.56
MS (70 eV): m/e (%)=154 (10.M⁺), 139 (100), 85 (11), 83 (24), 69 (58), 67 (11), 55 (22), 41 (23), 39 (14).

5b $R_t$=16.09
MS (70 eV): m/e (%)=154 (10.M⁺), 139 (100), 85 (9), 83 (22), 69 (53), 57 (10), 55 (18), 41 (18), 39 (11).

5a $^{13}$C-NMR $(CDCl_3)$, Varian VXR-300: [ppm]: 18.35, 22.33, 25.70 $(CH_3)$, 34.40, 40.83, 67.88 $(CH_2)$, 30.27, 74.62, 126.38, (CH), 135.05 (C).

5b $^{13}$C-NMR (CDCl$_3$), Varian VXR-300: [ppm]: 18.28, 19.24, 25.78 (CH$_3$), 32.54, 38.20, 62.11 (CH$_2$), 24.97, 69.10, 126.38, (CH), 135.05 (C).
B R$_t$=15.12
MS (70 eV): M/E (%)=154 (35.M$^+$), 139 (100), 83 (21), 71 (49), 69 (60), 67 (23), 55 (64), 41 (78).
R$_t$=15.21
MS (70 eV): m/e (%)=154 (37.M$^+$), 139 (100), 83 (22), 71 (50), 69 (68), 67 (24), 55 (63), 41 (80).

EXAMPLE 5
Production of Racemic cis/trans-rose oxide (5a+5b) [9:1]
Variant C In a 1 liter stirrer with drop funnel, thermometer, water separator and return flow cooler 600 ml cyclohexane and 50 g (0.27 mol) diol mixture 3a/b (from Example 2) were added in with mixing under return flow. Subsequently over a period of 2 hours a total of 5 g (1.74 mmol) of tungstate silicic acid hydrate were added stepwise and subsequently stirred for an additional 2 hours with return flow. During this time a total of 4.3 ml of water were distilled off. After cooling off to room temperature neutralization with sodium solution and washing with water were carried out. After the drying over Na$_2$SO$_4$ the solvent was distilled off under reduced pressure.

There remained 40 g raw product (racemic cis/trans-rose oxide (5a+5b)).
GC (Conditions see Example 2): 5a (62.9%); 5b (6.0%); B=0.9%
Σ 5a+5b=68.9%
5a:5b=91:9
Distillation through a 30 cm metal packed column produced 21.9 g
Kp$_{20mbar}$ 79°–81° C.
This corresponded to a yield of 58.7%.
GC (Conditions see Example 2): 5a (90.5%); 5b (8.1%); B=0.25%
Σ 5a+5b=98.6%
5a:5b=92:8
D 20/4=0.8707
n 20/D=1.4550
[α] 20/D=0.0°
GC/MS: Conditions see Example 3
5a R$_t$=15.59
MS (70 eV): m/e (%)=154 (12.M$^+$), 139 (100), 85 (10), 83 (23), 69 (55), 67 (10), 55 (21), 41 (21), 39 (13).
5b R$_t$=16.09
MS (70 eV): m/e (%)=154 (10.M$^+$), 139 (100), 85 (10), 83 (23), 69 (59), 67 (12), 55 (22), 41 (22), 39 (12)
5a $^{13}$C-NMR (CDCl$_3$), Varian VXR-300: [ppm]: 18.35, 22.34, 25.70 (CH$_3$), 34.46, 40.85, 67.87 (CH$_2$), 30.29, 74.62, 126.44 (CH), 134.95 (C).
5b $^{13}$C-NMR (CDCl$_3$), Varian VXR-300: [ppm]: 18.27, 19.23, 25.78 (CH$_3$), 32.54, 38.20, 62.11 (CH$_2$), 24.97, 69.10, 125.36 (CH), 135.44 (C).
B R$_t$=15.12
MS (70 eV): m/e (%)=154 (35.M$^+$), 139 (100), 83 (22), 71 (50), 69 (61), 67 (23), 55 (64), 41 (79).
R$_t$=15.21
MS (70 eV): m/e (%)=154 (10.M$^+$), 139 (100), 83 (23), 71 (49), 69 (68), 67 (25), 55 (62), 41 (80).

EXAMPLE 6
Production of Racemic cis/trans-rose oxide (5a/b) [9:1]
Variant D

In a 1 liter stirrer with drop funnel, thermometer and return flow cooler 100 g toluol, 0.5 g tetrabutyl ammonium hydrogen sulfate, 25 g H$_3$PO$_4$ 85% and 60 g (0.32 mol) diol-mixture (from Example 2) were added with mixing over a period of 10 minutes with return flow, cooled to room temperature, the organic phase separated off, washed neutral with soda solution, dried over sodium sulfate and the solvent distilled off under reduced pressure.

There remain 49.8 g raw product (racemic cis/trans-rose oxide (5a/b)).
GC (Conditions see Example 2): 5a (63.7%); 5b (5.9%); B (0.9%)
Σ 5a+5b=69.6%
5a:5b=91:9
Distillation over a 30 cm metal packed column produced 26.36 kg KP$_{20mbar}$=78°–80° C. This corresponds to a yield of 58.9%.
GC (Conditions see Example 2): 5a (90.1%); 5b (7.5%); B=0.76%
Σ 5a+5b=97.6%
5a:5b=92:8
D 20/4=0.8698
n 20/D=1.4531
[α] 20/D=0.0°
GC/MS: Conditions see Example 3
5a R$_t$=15.57
MS (70 eV): m/e (%)=154 (14.M$^+$), 139 (100), 85 (11), 83 (27), 69 (59), 67 (10), 55 (26), 41 (22), 39 (14).
5b R$_t$=16.10
MS (70 eV): m/e (%)=154 (11.M$^+$), 139 (100), 85 (10), 83 (25), 69 (58), 67 (10), 55 (26), 41 (19), 39 (13).
5a $^{13}$C-NMR (CDCl$_3$), Varian VXR-300: [ppm]: 18.35, 22.34, 25.71 (CH$_3$), 34.44, 40.84, 67.87 (CH$_2$), 30.28, 74.61, 126.44, (CH), 134.94 (C).
5b $^{13}$C-NMR (CDCl$_3$), Varian VXR-300: [ppm]: 18.29, 19.25, 25.79 (CH$_3$), 32.55, 38.21, 62.12 (CH$_2$), 24.97, 69.11, 125.37, (CH), 135.46 (C).
B R$_t$=15.12
MS (70 eV): M/E (%)=154 (36.M$^+$), 139 (100), 83 (24), 71 (53), 69 (60), 67 (25), 55 (67), 41 (77).
R$_t$=15.20
MS (70 eV): m/e (%)=154 (36.M$^+$), 139 (100), 83 (21), 71 (51), 69 (68), 67 (25), 55 (60), 41 (78).

EXAMPLE 7
Production of (−)-3,7-Dimethyl-oct-5-en-1,7-diol and (1)-3,7-Dimethyl-oct-7-en-1,6-diol 112 g (0.72 mol) (−)-Citronellol [n 20/D=1.4546; D 20/4=0.8735; [α] 20/D=−23.1°]; (GC-Conditions see Example 2, R$_t$=5.1', 92.1%) were converted in an illumination device (according to Example 1) with subsequent reduction of the hydroperoxide-solution (according to Example 2) into a mixture of optically active (−)-3,7-dimethyl-oct-5-en-1,7-diol and (−)-3,7-dimethyl-oct-7-en-1,6-diol. There remained 149 g raw product.
GC (Conditions according to Example 2)
(−)-3,7-dimethyl-oct-5-en-1,7-diol R$_t$=7.6' (44.3%)
(−)-3,7-dimethyl-oct-7-en-1,6-diol R$_t$=8.5' (43.9%)

EXAMPLE 8
Production of (−)-Cis/trans-rose oxide

Under the process conditions according to Example 3 (Variant A) 15.8 g raw product were obtained from 20 g (0.1 mol) diol-mixture (from Example 7) (GC- Conditions see Example 2).
(−)-cis-rose oxide 64.4%
(−)-trans-rose oxide 7.0%
cis+trans=71.4%
cis:trans=90:10
Distillation through rotation band column produced 8.91 g Kp$_{22mbar}$=80–81° C., which corresponds to a yield of 59.1%.
(−)-cis-rose oxide: (−)-trans-rose oxide=9:1
D 20/4=0.8755
n 20/D=1.4562
[α] 20/D=−25.6°
GC/MS-, $^{13}$C-NMR- as well as $^1$H-NMR-Data are in agreement with the natural isolate.

EXAMPLE 9
Production of a Mixture of (+)-3,7-Dimethyl-oct-5-en-1,7-diol and (+)-3,7-Dimethyl-oct-7-en-1,6-diol 112 g (0.72 mol) (+)-Citronellol [n 20/D=1.4547, D 20/4=0.8732, [α] D/20=+3.5'], GC-Conditions see Example 2), $R_r$=6.1' (92.4%) were converted in an illumination device (according to Example 1) with a subsequent $Na_2SO_3/H_2O$-reaction of the hydroperoxide-solution (according to Example 2) into a mixture of optically active (+)-3,7-dimethyl-oct-5-en-1,7-diol and (+)-3,7-dimethyl-oct-7-en-1,6-diol.

There remained 152 g raw product.
GC (Conditions see Example 2)
(+)-3,7-dimethyl-oct-5-en-1,7-diol $R_r$=7.6' (45.1%)
(+)-3,7-dimethyl-oct-7-en-1,6-diol $R_r$=8.5' (44.2%)

EXAMPLE 10
Production of (+)-Cis/trans-rose oxide

Under the process conditions according to Example 3 (Variant A) 15.9 g raw product were obtained from 20 g (0.1 mol) diol mixture (from Example 9).
GC (Conditions see Example 2):
(+)-cis-rose oxide=62.9%; (+)-trans-rose oxide=8.5%
cis+trans Rose oxide=71.4%
cis:trans=88:12

A distillation through a rotation band column produces 9.06 g $Kp_{22mbar}$=80–81° C. This corresponds to a yield of 60.1%.
GC (Conditions see Example 2):
(+)-cis-Rose oxide=90.1%;
(+)-trans-Rose oxide=8.2%
cis+trans Rose oxide: 98.3%
cis:trans=91.5:8.5
D 20/4=0.8735
n 20/D=1.4549
[α] 20/D=+24.1°
GC/MS-Data correspond to the natural isolate.

EXAMPLE 11
Production of Racemic 3,7-Dimethyl-oct-7-en-1,6-diol (3b)

According to the synthesis described in L. -F. Tietze et al. [L. -F. Tietze, Th. Eicher, 428–430, (1981), Jord. Stein Publishers, Stuttgart, N.Y.] one obtains in the manufacture of rose oxide the 3,7-dimethyl-oct-7-en-1,6-diol 3b as higher boiling point component.

Beginning with the mixture described in Example 1 for production of citronellyl-hydroperoxide (2a/b), which after reduction under the conditions set forth in Example 2 were converted to a mixture of the racemic diol 3a/b, one obtains by acidic cyclization according to the method described in L. -F. Tietze, Th. Eicher a mixture of the two cis/trans-Rose oxide (5a/b) as well as the not converted 3,7-dimethyl-oct-7-en-1,6-diol (3b).

So one obtained beginning with 112 g (0.72 mol) citronellol synthetically after reduction and cyclization 105 g raw product.
GC (Conditions see Example 2): 5a (30.5%); 5b (9.3%); 3b (40.1%).
Distillation via a 30 cm metal packed column produced 36.8 g $KP_{2mbar}$ 115–118° C. of the substance 3b (91%).

EXAMPLE 12
(Non-inventive Example for Comparison to Inventive Examples 13 and 14)
Production of racemic cis/trans-rose oxide (5a+5b) [9:1]

In a 500 ml stirrer with drop funnel, thermometer and return flow cooler, 100 g toluol, 3.5 g 50% sulfuric acid and 20 g (0.1 mol) 3,7-dimethyl-oct-7-en-1,6-diol 3b (from Example 11) were stirred for 60 minutes under return flow, cooled to room temperature, the organic phase separated off, washed to neutral with soda solution and water, dried over sodium sulfate and the solvent distilled off under reduced pressure. Herein no allylether was employed.

There remains 17.2 g raw product
GC (Conditions see Example 2): 5a (15.1%); 5b (1.6%); B 1.8%
Σ 5a+5b=16.7%
5a:5b=91:9
Distillation through a rotating-strip column produced 1.6 g $KP_{22mbar}$=79–81° C. of the racemic mixture of the substances (5a/5b). This corresponds to a yield of 10.1%.
GC (Conditions see Example 2): 5a (90.1%); 5b (7.3%); B 1.8%
Σ 5a+5b=97.4%
5a:5b=92.5:7.5
D 20/4=0.8687
n 20/D=1.4543
[α]20/D=0.1°

EXAMPLE 13
Production of Racemic Cis/trans-Rose Oxide (5a+5b) [9:1]

In a 1 liter stirrer with drop funnel, thermometer and return flow cooler and water separator 15.0 g (0.078 mol) 3,7-dimethyl-oct-7-en-1,6-diol (3b) (from Example 11), 500 ml cyclohexane, 1 g Filtrol® and 8.9 g (0.078 mol) 4-methoxy-2-methyl-2-pentene (as an example of an allylether) were added in with mixing over a time of 9 hours. During this time a total of 0.7 ml $H_2O$ were separated off.

After cooling off to room temperature the Filtrol® is filtered off and the organic phase is washed to neutral with a soda solution and water, dried over $Na_2SO_4$ and the solvent distilled off under reduced pressure. There remained 12 g raw product.
GC (Conditions see Example 2): 5a (38.4%); 5b (4.3%); B=1.6%
Σ 5a+5b=42.7%
5a:5b=90:10
Distillation through a rotating-strip column produced 3.15 g
$KP_{23mbar}$=81–82.5° C. This corresponds to a yield of 26.3%.
GC (Conditions see Example 2:) 5a (90.3%); 5b (7.8%); B=1.6%
Σ 5a+5b=98.1%
5a:5b=90:10
D 20/4=0.8701
n 20/D=1.4536
[α]20/D=0.1°

EXAMPLE 14
Production of Racemic Cis/trans-Rose Oxide (5a+5b)[92:8]

In a 1 liter stirrer with thermometer, return flow cooler and water separator 15 g (0.078 mol) 3,7-dimethyl-oct-7-en-1, 6-diol (3b) (from Example 11) 500 ml cyclohexane, 1 g Filtrol® and 12 g (0.078 mol) cis/trans-rose oxide 5a/b (from Example 3) were added with stirring over a time of 10 hours under return circulation (note: the cis/trans-rose oxide 5a/b, which was added in an equimolar amount with respect to the diol 3b, is a particularly preferred allylether). During this time 1.1 ml $H_2O$ were separated off. After cooling to room temperature the Filtrol® was filtered off and the organic phase was washed to neutral with soda solution, dried over $Na_2SO_4$ and the solvent distilled off under reduced pressure. There remained 25 g raw product.
GC (Conditions see Example 2): 5a (70.3%); 5b (5.8%); B=1.0%
Σ 5a+5b=76.1%
5a:5b=92:8
Distillation through a rotating-strip column yielded 18.1 g $KP_{22mbar}$=79–81° C. This corresponds to a yield of 6.1 g=50.8%.
GC (Conditions see Example 2): 5a (90.1%); 5b (7.6%); B=0.9%

Σ 5a+5b=97.7%

5a:5b=92:8

D 20/4=0.8700 n 20/D=1.4534

[α]20/D=0.1°

A comparison of Examples 12, 13 and 14 showed a significant yield reduction between the non-inventive (comparative) Example 12 and the inventive Examples 13 and 14, as well as a likewise significant decrease between the inventive Examples 13 and 14. Rose oxide is accordingly particularly suitable as allylether component.

Examples according Examples 11–14 were carried out with a likewise appropriate optically active adduct species (Citronellol, Citronellyl-Hydroperoxide, diol 3b). There were produced respectively analogous results.

What is claimed is:

1. A process for production of rose oxide of General Formula A,

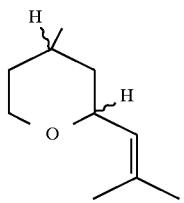

said process comprising treating 3,7-dimethyl-oct-7-en-1,6-diol (3b) alone or in mixture with [3,7-dimethyl-oct-7-en-1,7-diol] 3,7-dimethyl-oct-5-en-1,7-diol (3a) with acid in the presence of an allylether, wherein when said acid treatment occurs in a two phase liquid/liquid system it occurs under the control of a phase transfer catalyst and wherein when said acid treatment occurs in a two phase liquid/solid system it occurs by means of a solid carrier bound acid.

2. A process for production of rose oxide of General Formula A,

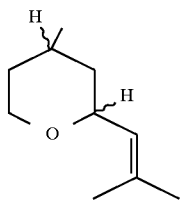

said process comprising treating 3,7-dimethyl-oct-7-en-1,6-diol (3b) alone or in mixture with 3,7-dimethyl-oct-5-en-1,7-diol (3a) with acid in the presence of an allylether, wherein when said acid treatment occurs in a two phase liquid/liquid system it occurs under the control of a phase transfer catalyst and wherein when said acid treatment occurs in a two phase liquid/solid system it occurs by means of a solid carrier bound acid, wherein said allylether is formed in situ upon addition of acid.

3. A process for production of rose oxide of General Formula A,

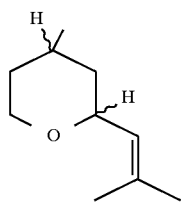

said process comprising treating 3,7-dimethyl-oct-7-en-1,6-diol (3b) alone or in mixture with 3,7-dimethyl-oct-5-en-1,7-diol (3a) with acid in the presence of an allylether, wherein when said acid treatment occurs in a two phase liquid/liquid system it occurs under the control of a phase transfer catalyst and wherein when said acid treatment occurs in a two phase liquid/solid system it occurs by means of a solid carrier bound acid, wherein said allylether is a rose oxide.

4. The process according to claim 3, wherein said rose oxide is mixed into the 3,7-dimethyl-oct-7-en-1,6-diol (3b) before or during said acid treatment.

5. The process according to claim 1, wherein said 3,7-dimethyl-oct-7-en-1,6-diol (3b) is subject to said acid treatment while in mixture with 3,7-dimethyl-oct-5-en-1,7-diol (3a).

6. The process according to claim 5, wherein said rose oxide is formed in situ during said acid treatment from the 3,7-dimethyl-oct-5-en-1,7-diol (3a).

7. The process according to claim 1, wherein acid treatment employs sulfuric acid, phosphoric acid, an acid activated calcium montmorillonite or a hetropolytungstinic acid.

8. The process according to claim 7, wherein said hetropolytungstinic acid is tungstate silicic acid or tungstate phosphoric acid.

9. The process according claim 1, wherein said mixture of diols (3a) and (3b) is obtained from citronellol of General Formula (1) by photochemical sensitized singlet-oxygen-oxidation and subsequent reduction of the obtained hydroperoxide (2a+2b).

10. The process according to claim 1, wherein said diol (3b) or said diol mixture (3a+3b) is dissolved in an aprotic solvent.

11. The process according to claim 1, wherein the 3,7-dimethyl-oct-7-en-1,6-diol (3b) or mixture with the diol (3a), is mixed with a more than necessary amount of rose oxide.

12. The process according to claim 1, wherein said acid treatment is carried out under addition of a phase transfer catalyst selected from methyltrioctylammonium chloride, tetrabutyl ammonium-chloride, tetrabutyl ammonium-bromide or tetrabutyl ammonium hydrogen sulfate in concentrations of 0.1 weight % to 10 weight % based on the amount of the employed diol mixture (3a+3b) or diol (3b).

13. The process according to claim 12, wherein the concentration of said a phase transfer catalyst is from 4–6 weight % based on the amount of the employed diol mixture (3a+3b) or diol (3b).

14. The process according to claim 11, wherein for acid treatment of the diol mixture (3a+3b) or the diol (3b) a conventional activated calcium montmorillonite and acid-activated natural calcium bentonite is employed in a concentration of 0.5 to 40 weight % based on the amount of the diol mixture (3a+3b) or diol (3b).

15. The process according to claim 14, wherein said conventional activated calcium montmorillonite is employed in a concentration of from 1–20 weight % based on the amount of the diol mixture (3a+3b) or diol (3b).

* * * * *